(12) United States Patent
White et al.

(10) Patent No.: US 6,534,677 B1
(45) Date of Patent: Mar. 18, 2003

(54) NON-CRUSHABLE, NON-FRIABLE, NON-BREAKABLE CARBON CATALYST SUPPORTS

(75) Inventors: James Ferguson White, Twinsburg, OH (US); Jeffrey James Ramler, Cleveland Heights, OH (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 09/873,680

(22) Filed: Jun. 4, 2001

(51) Int. Cl.$^7$ .......................... C07C 51/42; C07C 67/48
(52) U.S. Cl. .......................... 562/486; 560/78; 560/80; 526/912; 526/318.1; 526/318.2
(58) Field of Search ................ 562/486, 485; 560/78, 80

(56) References Cited

U.S. PATENT DOCUMENTS

| | | |
|---|---|---|
| 2,409,494 A | 10/1946 | Keating |
| 2,611,750 A | 9/1952 | White |
| 2,976,253 A | 3/1961 | Edwards et al. ............ 252/430 |
| 3,084,394 A | 4/1963 | Bickerdike et al. |
| 3,109,712 A | 11/1963 | Redfern |
| 3,171,720 A | 3/1965 | Shea, Jr. et al. |
| 3,198,714 A | 8/1965 | Johnson et al. |
| 3,310,611 A | 3/1967 | Zocher |
| 3,342,555 A | 9/1967 | McMillan |
| 3,345,440 A | 10/1967 | Googin et al. |
| 3,352,788 A | 11/1967 | Conlisk |
| 3,387,940 A | 6/1968 | McHenry et al. |
| 3,446,593 A | 5/1969 | Mostssd |
| 3,446,865 A | 5/1969 | Roth et al. |
| 3,544,502 A | 12/1970 | Boyer et al. |
| 3,565,980 A | 2/1971 | Otani |
| 3,574,548 A | 4/1971 | Sands et al. |
| 3,608,170 A | 9/1971 | Larson et al. |
| 3,626,042 A | 12/1971 | Appleby et al. |
| 3,628,984 A | 12/1971 | Ishlkawa et al. |
| 3,634,569 A | 1/1972 | Emanuelson et al. |
| 3,635,676 A | 1/1972 | Sands |
| 3,657,166 A | 4/1972 | Caldwell |
| 3,663,171 A | 5/1972 | Granger |
| 3,775,078 A | 11/1973 | Elmer et al. |
| 3,859,421 A | 1/1975 | Hucke |
| 3,964,933 A | 6/1976 | Fung et al. |
| 4,029,567 A | 6/1977 | Farnand et al. |
| 4,082,694 A | 4/1978 | Wennerberg et al. |
| 4,206,078 A | 6/1980 | Ohorodnik et al. |
| 4,235,748 A | 11/1980 | Berchielli et al. ............ 252/430 |
| 4,263,268 A | 4/1981 | Knox et al. |
| 4,329,260 A | 5/1982 | Lester et al. |
| 4,579,689 A | 4/1986 | Hershman et al. ........ 260/502.5 |
| 4,603,119 A | 7/1986 | Karl et al. |
| 4,668,496 A | 5/1987 | Korb et al. |
| 4,892,972 A | 1/1990 | Schroeder et al. |
| 4,987,116 A | 1/1991 | Karl et al. |
| 5,362,908 A | 11/1994 | Schroeder et al. |
| 5,616,792 A | 4/1997 | Bartos et al. |
| 5,723,659 A | 3/1998 | White ........................ 562/485 |
| 5,756,833 A | 5/1998 | Rosen et al. |
| 5,998,325 A | 12/1999 | Shepodd .................... 502/151 |

FOREIGN PATENT DOCUMENTS

EP 0316159 11/1988 ............ B01J/37/00

*Primary Examiner*—Paul J. Killos
(74) *Attorney, Agent, or Firm*—Raymond F. Keller

(57) ABSTRACT

The present invention provides a carbon-containing catalyst support that includes at least a carbonaceous material nd a thermosetting or sinterable polymer. The components are mixed and the polymer sintered or thermoset to provide a non-crushable, non-friable, and non-breakable composite. A catalytically active metal can be supported on the carbonaceous material prior to mixing, or on the composite after mixing and heating the mixture to sinter or thermoset the polymer.

38 Claims, No Drawings

NON-CRUSHABLE, NON-FRIABLE, NON-BREAKABLE CARBON CATALYST SUPPORTS

TECHNICAL FIELD

The present invention generally relates to catalyst supports, catalyst composites containing the catalyst supports, and methods of making and employing the catalyst supports and catalyst composites. The present invention particularly relates to catalyst materials and methods associated with the purification of terephthalic acid.

BACKGROUND OF THE INVENTION

Catalytic processes are indispensable in the chemical industry. Frequently, catalytic processes employ a catalyst that is incorporated on a support. Effective use of the catalyst often corresponds to the quality of the catalyst support. Poor quality catalyst supports, due to at least one of physical degradation, chemical degradation, undesirable properties, and inconsistent properties, limit the effectiveness of catalysts incorporated therein. Conditions such as high temperatures, high pressures, and high or low pH present challenges to the integrity of catalyst supports.

For example, conventional catalyst composites for the purification of terephthalic acid by the Amoco mid-continent process (PTA catalysts) are composed of palladium supported on granular 4×8 mesh carbon. These catalyst composites are designed to remove the two major impurities present in crude terephthalic acid: namely, yellow color and 4-carboxy benzaldehyde.

Carbon is the preferred support material for conventional PTA catalysts because it is essentially the only readily available material that can simultaneously yield an effective catalyst for color removal, 4-carboxy benzaldehyde removal, and also withstand the extremely corrosive environment of the terephthalic acid purification process. Although conventional carbon supported PTA catalysts have been used extensively over the past 20 years, such catalyst composites suffer from several well known disadvantages. These disadvantages include: highly irregular shapes leading to possible maldistribution of liquid or gas flows in a catalytic reactor bed utilizing such catalyst composites; shapes having sharp and fragile edges and corners, which tend to break off and contaminate the PTA product with undesirable dust and black particles; brittleness, which also leads to breakage and dust/black particles contaminating the PTA product; natural origin, i.e., coconut shell, which leads to nonuniformity from one growing season to another and consequent inconsistency of the carbon support; and being commonly derived from nutshells, such activated carbon has very small pores, leading to the requirement of locating all of the active catalytic metal near the external surface of the particles, where the metal is undesirably susceptible to loss during movement and abrasion that occurs during shipping and handling.

Non-carbon catalyst supports have been employed in catalytic processes in attempts to overcome the disadvantages associated with conventional carbon supported catalysts. Non-carbon catalyst supports include alumina supports, silica supports, alumina-silica supports, various clay supports, titania, and zirconium supports. However, there are at least one of several disadvantages associated with non-carbon catalyst supports: namely, that they may loose physical strength, that they are dissolved in corrosive environments (such as hot aqueous solutions of terephthalic acid) and that catalysts made using such supports have difficulties in removing undesirable color from crude terephthalic acid.

Improved catalyst supports and catalyst composites are therefore desired. Specifically, improved PTA catalyst supports and PTA catalyst composites are desired to provide improved methods of purifying terephthalic acid.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

The present invention is designed to address at least one of and preferably all of the above described disadvantages by providing a carbon-containing catalyst support that includes at least a carbonaceous material and a polymer. The components are mixed and the polymer sintered or thermoset to provide a non-crushable, non-friable, and non-breakable composite. A catalytically active metal can be supported on the carbonaceous material prior to mixing, or on the composite after mixing and heating the mixture to sinter or thermoset the polymer.

In one embodiment, the present invention relates to a catalyst support including a formed mixture of at least about 5% by weight of an activated carbonaceous material and at least about 5% by weight of a polymer sintered or thermoset after mixing with the carbonaceous material.

In another embodiment, the present invention relates to a catalyst composite including a catalyst support having at least about 5% by weight of an activated carbonaceous material and at least about 5% by weight of a sinterable or thermosetting polymer, and at least about 0.05% by weight of a catalytically active metal supported on the catalyst support.

In yet another embodiment, the present invention relates to a method of making a catalyst composite that includes mixing a carbonaceous material with a sinterable or thermosetting polymer to obtain a mixture, heating the mixture to sinter or thermoset the polymer and obtain a catalyst support, and supporting a catalytically active metal on the catalyst support to obtain a catalyst composite.

In a further embodiment, the present invention relates to a method of making a catalyst composite that includes supporting a catalytically active metal on a carbonaceous material, mixing the carbonaceous material, having the catalytically active metal supported thereon, with a sinterable or thermosetting polymer to form a mixture, and heating the mixture to sinter or thermoset the polymer.

Other advantages and novel features of the invention will become apparent from the following detailed description of the invention. The detailed description provides certain illustrative examples of the invention. These examples are indicative of but a few of the various ways in which the principles of the invention can be employed.

DETAILED DESCRIPTION OF THE INVENTION

In one embodiment, the present invention involves the preparation of a carbon/polymer catalyst support. The catalyst support is particularly suited for supporting catalytically active metals. The process involves mixing a carbonaceous material, a sinterable or thermosetting polymer, and optional additives. The mixture is preferably pressed or extruded into a suitable form, such as a monolith or particle shape. After or while forming, the mixture is heated to cause the polymer to sinter or thermoset, whereby the catalyst support becomes hard, coherent, and non-crushable. The mixture can be treated to support a catalyst thereto. The resulting catalyst composite can be employed in catalytic processes, such as in the purification of crude terephthalic acid.

One component of the catalyst support is a sinterable or thermosetting polymer. A sinterable polymer is one that becomes coherent by heating without melting. A thermosetting polymer is one that solidifies or "sets" irreversibly upon heating. Is should be noted that the categories of sinterable and thermosetting polymers are not mutually exclusive. The polymer can be any suitable polymer or mixture of polymers. Examples of sinterable polymers include fluorocarbon polymers, such as PTFE and TFE, polyolefins, such as poly-pentene-1,polypropylene, and polyethylene, polystyrene, substituted polystyrenes, polyesters, polyamides, epoxys, and polyethers. Examples of thermosetting polymers include phenolics, alkyds, amino resins, polyesters, epoxides, and silicones, as well as materials in which additive induced cross linking is possible, e.g., natural rubber. Preferably, the thermosetting or sinterable polymer is chemically resistant to the extent that the thermosetting or sinterable polymer can be employed in a terephthalic acid purification process. In general, fluorocarbon polymers have this type of chemical resistance.

In one embodiment, the thermosetting or sinterable polymer constitutes at least about 5% by weight of the catalyst support. In another embodiment, the thermosetting or sinterable polymer constitutes at least about 20% by weight of the catalyst support. In yet another embodiment, the thermosetting or sinterable polymer constitutes at least about 50% by weight of the catalyst support. In a still further embodiment, the thermosetting or sinterable polymer constitutes at least about 80% by weight of the catalyst support. Generally, the catalyst support comprises sufficient thermosetting or sinterable polymer to render the composite non-friable after forming and thermosetting or sintering.

The thermosetting or sinterable polymer is combined with a carbonaceous material in forming the catalyst support. The carbonaceous material may be derived from any suitable carbon source. The carbonaceous material initially combined with the polymer is generally an activated carbon, although it is conceivable that a non-activated carbon may be converted to activated carbon at some point after combination with the polymer. Carbonaceous materials include activated carbon derived from coal, lignite, wood, nutshells, bio waste, peat, pitches, and cokes; and non-activated carbon derived from carbon char powder (e.g. charcoal).

The carbonaceous material combined with the polymer is typically in powder form. In one embodiment, the carbonaceous material has a particle size (average particle size) of less than about 1 millimeter. In another embodiment, the carbonaceous material has a particle size of less than about 200 microns. In yet another embodiment, the carbonaceous material has a particle size of less than about 50 microns. In still yet another embodiment, the carbonaceous material has a particle size of less than about 25 microns.

Activated carbonaceous materials are commercially available or they may be made. For example, activated carbonaceous materials may be made by heating coal, coke, lignite, graphite, bone, wood, nut shells including coconut shells, bio waste, and sugar. The source of carbonaceous materials is not critical to the present invention. Consequently, another advantage associated with the present invention is that the source of carbonaceous materials is not critical. U.S. Pat. Nos. 3,084,394; 3,109,712; 3,171,720; 3,198,714; 3,310,611; 3,387,940; 3,342,555; 3,345,440; 3,352,788; 3,446,593; 3,565,980; 3,574,548; 3,626,042; 3,628,984; 3,634,569; 3,635,676; 3,663,171; 3,859,421; 4,029,567; 4,082,694; 4,206,078; 4,263,268; 4,329,260; 4,603,119; 4,668,496; 4,954,469; 4,987,116; describe various carbonaceous materials and are hereby incorporated by reference in this regard.

In one embodiment, the polymer/carbon catalyst support contains at least about 5% carbonaceous material by weight. In another embodiment, the polymer/carbon catalyst support contains at least about 10% carbonaceous material by weight. In yet another embodiment, the polymer/carbon catalyst support contains at least about 20% carbonaceous material by weight. In still yet another embodiment, the polymer/carbon catalyst support contains at least about 30% carbonaceous material by weight.

In one embodiment, the surface area of the activated carbonaceous material is in the range from about 200 $m^2/g$ to about 1,600 $m^2/g$. In another embodiment, the surface area of the activated carbonaceous material is in the range from about 800 $m^2/g$ to about 1,300 $m^2/g$.

The thermosetting or sinterable polymer and carbonaceous material are combined together, optionally with one or more additives. Additives include any material that facilitates mixing and subsequent forming. Additives include rheology control agents, extrusion aids, suspension agents, surfactants, water, and low boiling organic compounds. Rheology control agents include cellulose ethers, polyvinyl alcohols, and polyalkylene oxides. Examples of cellulose ethers include sodium carboxymethylcellulose (CMC), hydroxyethylcellulose (HEC), methylcellulose (MC) and derivatives thereof. Extrusion aids include glycol compounds, such as polyalkylene glycols.

After combining at least the carbonaceous material, the thermosetting or sinterable polymer, and any additives, the mixed material is formed into a suitable shape. The shape substantially corresponds to the shape of the resultant catalyst support. Examples of shape for the formed material include spheres, tablets, cylinders, stars, tri-lobes, quadra-lobes, pellets, granules, honeycombs, and cubes. The shapes, generally referred to as "particulate", may have any suitable size. However, in a preferred embodiment, the sizes of the particles are substantially uniform. In a preferred embodiment, the mixed material is formed into cylindrical shapes having diameters from about 1.5 mm to about 3.5 mm. In another preferred embodiment, the mixed material is extrudable in a continuous manner over a broad range of diameters and shapes.

The mixed material can be formed into a desired shape with any suitable equipment and technique. Examples of forming techniques include tableting, extrusion, pan agglomeration, pelleting, roll compaction, and briquetting. Examples of forming machines include molding machines, tableting machines, extrusion molding machines, rolling granulators, marumarizers, and pelletors. The mixture can be formed either with or without the application of heat. In a preferred embodiment, the mixture is formed with a machine that does not supply heat, such as a pellet machine of the type commonly used in the animal food industry, a California Pellet Mill, for example, or a tabletting press.

The formed material has the polymer and the carbonaceous material uniformly mixed therein. Uniformly mixing the polymer and carbonaceous material contributes to the advantageous properties of the resultant catalyst support and catalyst composite.

The formed (shaped) material is heat treated to cause the polymer to sinter or thermoset. This heat treatment can be applied while forming the pellets. In a preferred embodiment, however, heat treatment takes place after the mixture is formed. For heat treatment, a furnace is generally employed. The heat treatment time and temperature depend on the identity of the thermosetting or sinterable polymer. In one embodiment, the heat treatment temperature is from about 200 to about 400° C. In another embodiment, the heat treatment temperature is from about 225 to about 275° C. In a further embodiment, the heat treatment temperature is from about 350 to about 400° C.

The resultant polymer/carbon catalyst supports do not crush and break when subjected to forces commonly used to test crush strength, as in ASTM method D4179. Rather, the supports deform. If the supports are deformed to about 75% of their original size in one dimension, they generally can return to their original shape within a few hours or days. Larger deformations, involving compression to 25–40% of original size, often do not reverse. However, the supports flatten rather than crush or break. The supports are therefore noncrushable, non-friable, and non-breakable.

A crush strength for catalyst supports; of the invention can be defined as the force required to deform a cylindrical particle of the support to 80% of its original diameter. In one embodiment, the supports have a crush strength of at least about 1 lb/mm particle length. In another embodiment, the supports have a crush strength of at least about 3 lbs/mm particle length. In a further embodiment, the supports have a crush strength of at least about 6 lbs/mm particle length. In yet another embodiment, the supports have a diameter from about 1 to about 10 mm and a crush strength according to one of the foregoing embodiments.

In one embodiment, the polymer/carbon catalyst supports of the present invention have a porosity (water absorption pore volume) from about 0.15 to about 0.5 cc $H_2O$ abs/g support. In another embodiment, the polymer/carbon catalyst supports of the present invention have a porosity from about 0.20 to about 0.45 cc $H_2O$ abs/g support. In yet another embodiment, the polymer/carbon catalyst supports of the present invention have a porosity from about 0.35 to about 0.45 cc $H_2O$ abs/g support.

In one embodiment, the surface area of the polymer/carbon catalyst supports range from about 40 $m^2/g$ to about 1,500 $m^2/g$. In another embodiment, the surface area of the polymer/carbon catalyst supports range from about 200 $m^2/g$ to about 900 $m^2/g$.

In one embodiment of the present invention, a catalytically active metal is supported on the polymer/carbon catalyst support, thereby providing a catalyst composite. The metal can be supported on the carbon prior to combining the carbon with the polymer, although it is more common to impregnate the catalyst support with the metal after the support materials are mixed and formed.

The metal can be introduced to the support by any suitable means, including impregnating the catalyst support with a solution of at least one catalytically active metal. Impregnation is effected by treating the polymer/carbon catalyst support with an aqueous or organic solution of the desired metal or combination of metals in an amount sufficient to deposit at least one catalytically active metal on or near a surface of the support. Impregnation techniques include immersion techniques, spraying techniques, and incipient wetness techniques.

In one embodiment, the amount of catalytically active metal in the catalyst composite is from about 0.05% to about 30% by weight. In another embodiment, the amount of catalytically active metal in the catalyst composite is from about 0.2% to about 10% by weight. In yet another embodiment, the amount of catalytically active metal in the catalyst composite is from about 0.35% to about 5% by weight.

Catalytically active metals typically include precious metals. Examples of catalytically active metals and mixture of metals include platinum, platinum and rhenium, platinum and ruthenium, platinum and tungsten, platinum and nickel, platinum and tin, platinum and iron, platinum and copper, platinum and rhodium, platinum and lead, platinum and germanium, palladium, palladium and rhenium, palladium and rhodium, palladium and tungsten, palladium and nickel, palladium and tin, palladium and copper, palladium, and ruthenium, palladium and lead, palladium and germanium, cobalt, rhodium, ruthenium, osmium, iridium, various combinations thereof, etc. It is to be understood that the aforementioned list of catalytically active metals are only representative, and thus not limiting of the type of metals with which the catalytic support may be impregnated.

In one embodiment, the catalytically active metal provides the catalyst composite with a CO adsorption of at least about 50 microliters per gram catalyst composite at STP. In another embodiment, the catalytically active metal provides the catalyst composite with a CO adsorption of at least about 100 microliters per gram catalyst composite at STP. In a further embodiment, the catalytically active metal provides the catalyst composite with a CO adsorption of at least about 200 microliters per gram catalyst composite at STP.

The polymer/carbon catalyst supports and catalyst composites of the present invention are suitable for use in catalytic processes. Catalytic processes where the polymer/carbon catalyst supports and catalyst composites of the present invention can be employed include hydrogenation, rearrangement, purification, dehydration, dehydrogenation, oxidation, reduction, polymerization, dehydrocylcization, reforming, hydrocracking, and isomerization. The specific catalytic reactions/processes are too numerous to list, but the following are specific examples.

The catalyst composite of the present invention is suitable for use in purification of relatively impure or crude polycarboxylic aromatic acids, particularly crude terephthalic acid, isophthalic acid, phthalic acid and naphthalene dicarboxylic acid. The catalyst composite of the present invention is also suitable for use in purification of amines and alkynol amines, and particularly aromatic amines, aromatic alkynol amines, aliphatic amines, and aliphatic alkynol amines.

In one embodiment, the impure polycarboxylic aromatic acid is a crude product of the catalytic oxidation of an aromatic compound. Examples of suitable aromatic compounds include 1,2-dimethylnaphthalene; 2,6-dialkylnaphthalene; 2-acyl-6-alkylnaphthalene; 2,6-dimethylnaphthalene, 2,6-diethylnaphthalene; 2,6-diisopropylnaphthalene; 2-acetyl- 6-methylnaphthalene; 2-methyl-6-ethyl naphthalene; para-dialkylxylene; meta-dialkylxylene; and orthodialkylxylene; wherein the alkyl groups contain from 1 to about 6 carbon atoms. In a preferred embodiment, the crude acid purified in accordance with the present invention is at least one of terephthalic acid formed by the oxidation of para-xylene, isophthalic acid formed by the oxidation of meta-xylene and 2,6-naphthalene dicarboxylic acid formed by the oxidation of 2,6-dialkylnaphthalene (preferably 2,6-dimethyl naphthalene).

In another embodiment, the crude polycarboxylic aromatic acid, such as 2,6-naphthalene dicarboxylic acid, is made by esterification to form the corresponding ester, in this case dimethyl naphthalene dicarboxylate, and then hydrolyzation to form the polycarboxylic aromatic acid. In this embodiment, the ester can be purified prior to hydrolyzing to form the polycarboxylic aromatic acid.

Methods of catalytically purifying crude polycarboxylic aromatic acids including terephthalic acid are known. For example, U.S. Pat. No. 3,607,921; 3,887,613; 3,919,306; 4,260,817; 4,281,179; 4,317,923; 4,394,299; 4,415,479; 4,447,646; 4,605,763; 4,629,715; 4,791,226; 4,803,295; 4,808,751; 4,892,972; 4,937,378; 5,180,849; 5,362,908; 5,420,344; 5,616,192; 5,723,659; 5,756,833; describe various methods of catalytically purifying crude polycarboxylic aromatic acids and particularly terephthalic acid and are hereby incorporated by reference for their teachings in this regard. Methods of catalytically purifying crude amines and alkynol amines, and particularly aromatic amines and aromatic alkynol amines, are known. In this connection, the catalyst composite according to the present invention may be used in such methods.

In one embodiment, the catalyst support is contacted with an aqueous solution or relatively impure or crude terephthalic acid that includes relatively large amounts of impurities such as 4-carboxy benzaldehyde and undesirable coloring. Such impurities are typically present in amounts up to about 10,000 parts per million parts of terephthalic acid, by weight (although higher amounts are encountered in some instances). These impurities adversely affect subsequent terephthalic acid polymerization reactions to produce polyethylene terephthalate, as well as cause undesirable coloring of the resulting polyethyleneterephthalate polymers.

In this embodiment, the catalyst support is contacted with an aqueous solution of relatively impure or crude terephthalic acid at an elevated temperature and pressure in a fixed catalyst bed. The crude terephthalic acid to be purified is dissolved in water or a like polar solvent. Water is the preferred solvent; however, other suitable polar solvents include the relatively lower molecular weight alkyl carboxylic acids, alone or admixed with water.

In one embodiment, the temperature during catalytic purification is from about 50° C. to about 350° C. In another embodiment, the temperature during catalytic purification is from about 225° C. to about 340° C.

The pressure primarily depends upon the temperature at which the purification process is carried out. Inasmuch as the temperatures at which practical amounts of the impure terephthalic acid may be dissolved are substantially above the normal boiling point of the polar solvent, the pressures are necessarily considerably above atmospheric pressure to maintain the aqueous solution in liquid phase. If the reactor is hydraulically full, the reactor pressure can be controlled by the feed pumping rate. In one embodiment, the pressure during hydrogenation is from about 150 pounds per square inch gauge (psig) to about 1600 psig. In another embodiment, the pressure during hydrogenation is from about 900 psig to about 1,200 psig.

In the operating mode where process control is effected by adjusting the hydrogen partial pressure, the hydrogen partial pressure in the reactor is preferably from about 10 psig to about 800 psig. The hydrogen partial pressure can also be in the range from about 100 psig to about 600 psig. In some circumstances, higher partial pressures can be employed. The partial pressure range depends upon the service pressure rating of the reactor, the degree of contamination of the impure terephthalic acid, the activity and age of the particular catalyst employed, and like processing considerations.

When purifying impure or crude terephthalic acid, in one embodiment, the reactor atmosphere contains from about 10% to about 40% by weight hydrogen and from about 60% to about 90% by weight water vapor. In another embodiment, when purifying impure or crude terephthalic acid, the reactor atmosphere contains from about 15% to about 35% by weight hydrogen and from about 65% to about 85% by weight water vapor.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, an amount of hydrogen that is sufficient to effect the desired hydrogenation under the reaction conditions employed is supplied to the purification reactor.

In one embodiment, activity rates for the removal of 4-carboxy benzaldehyde with a 0.5% by weight Pd catalyst composites (made of Pd on the polymer/carbon catalyst supports) of the present invention are from about 0.5 $hr^{-1}$ to about 2.6 $hr^{-1}$. In another embodiment, activity rates for the removal of 4 carboxy benzaldehyde with a 0.5% by weight Pd catalyst composites of the present invention are from about 1.1 $hr^{-1}$ to about 2.2 $hr^{-1}$.

In one embodiment, the catalyst composites of the present invention remove at least about 75% of color from crude terephthalic acid. In another embodiment, the catalyst composites of the present invention remove at least about 80% of color from crude terephthalic acid. In yet another embodiment, the catalyst composites of the present invention remove at least about 90% of color from crude terephthalic acid.

The following examples illustrate the processes of the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

A mixture of 30% activated coconut carbon, 18×40 mesh, code L97-1-58, supplied by Pica Corp., and 70% PTFE powder, code Fluon G-311, supplied by ICI Fuoropolymers, is mixed and pressed into tablets approximately 3 mm in diameter and 3.5 mm in length with a continuous mechanical tabletter. The tablets are sintered by heating in air at a rate of 1.5° C. /min to 375° C. in a muffle furnace. After holding at 375° C. for 4 hours, the tablets are allowed to cool slowly over a period of 5 hours. The crush strength, measured by pressing a tablet between two parallel plates until the tablet has deformed to 80% of its original diameter, is 23 lbs/tablet. ASTM D-4058 attrition is measured at 0.1% , meaning that attrition effectively does not occur with these tablets.

EXAMPLE 2

3 mm diameter by 3.5 mm length tablets are formed from a mixture of 30% activated coconut carbon, 30×140 mesh, code PCB, supplied by Calgon Corp., and 70% TEFZEL HT-2190 TFE powder, supplied by Dupont Corp. The tablets are sintered as in Example 1, but with a peak temperature of 250° C. The resulting crush strength is 31 lbs/tablet. Reducing the sintering temperature to 240° C. results in tablets having a crush strength of 40 lbs/tablet.

EXAMPLE 3

3 mm diameter by 3.5 mm length tablets are formed from a mixture of 30% activated coconut carbon, 30×140 mesh, code PCB, supplied by Calgon Corp., and 70% PTFE powder, code 850A, supplied by Dupont Corp. The tablets are sintered as in Example 1. The resulting tablets do not crush and break when pressure is applied.

EXAMPLE 4

⅛ " diameter by ⅛ " length tablets are formed from a mixture of 30% activated coconut carbon, 30×140 mesh, code PCB, supplied by Calgon Corp., and 70% TEFZEL HT-2190 TFE powder Dupont Corp. The tablets are sintered as in Example 1, but with a peak temperature of 240° C. The resulting tablets do not crush and break when pressure is applied.

EXAMPLE 5

A mixture of 5% activated coconut carbon, all less than 325 mesh, code L6006, supplied by Pica Corp., and 95% PTFE powder, code Fluon G-311, supplied by ICI Fuoropolymers, is pressed into tablets approximately 3 mm in diameter and 3.5 mm in length with a continuous mechanical tabletter. The tablets are sintered by heating in air at a rate of 1.5° C. /min to 375° C. in a muffle furnace. After holding at 375° C. for 4 hours, the tablets are allowed to cool slowly over a period of 5 hours. Although these tablets are dustier than those of the other examples, they do not crush and break when pressure is applied. The crush strength is 17 lbs/tablet.

EXAMPLE 6

A 0.5% Pd catalyst is prepared by impregnating, via incipient wetness technique, 100 g of the tablets of Example 1 with sodium palladium chloride. The catalyst is reduced by pouring it into a 80° C. solution of 2.5 g sodium formate in 200 cc deionized water. Afterwards, the catalyst is washed to remove residual sodium, formate, and chloride ions. The resulting catalyst composite pellets do not crush and break when pressure is applied. CO adsorption is 238 microliters per gram palladium at STP.

EXAMPLE 7

A 0.5% Pd catalyst is prepared by impregnating, via incipient wetness technique, 100 g of the tablets of Example 1 with a mixture of sodium palladium chloride and sodium bicarbonate. The catalyst is reduced by pouring it into a room temperature solution of 0.6 g sodium borohydride in 150 cc deionized water. Afterwards, the catalyst is washed to remove residual sodium, borate, and chloride ions. The resulting catalyst composite pellets do not crush and break when pressure is applied. CO adsorption is 444 microliters per gram palladium at STP.

EXAMPLE 8

A 0.35% Pd catalyst is prepared by impregnating, via incipient wetness technique, 100 g of the tablets of Example 1 with a mixture of sodium palladium chloride and sodium bicarbonate. The catalyst is reduced by pouring it into a room temperature solution of 0.4 g sodium borohydrate in 150 cc deionized water. Afterwards, the catalyst is washed to remove residual sodium, borate, and chloride ions. The resulting catalyst composite pellets do not crush and break when pressure is applied. CO adsorption is 403 microliters per gram palladium at STP.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A catalyst support, comprising a formed mixture of:
   at least about 5% by weight of an activated carbonaceous material; and
   at least about 5% by weight of a polymer sintered or thermoset after mixing with the carbonaceous material.

2. The catalyst support of claim 1, wherein the mixture has a water absorption porosity of at least about 0.2 cc $H_2O$ per g support.

3. The catalyst support of claim 1, wherein the catalyst support can be deformed to 80% of its original size in at least one of its dimensions without breaking.

4. The catalyst support of claim 1, wherein the polymer is sintered after mixing with the carbonaceous material.

5. A catalyst composite, comprising:
   a catalyst support comprising
      at least about 5% by weight of an activated carbonaceous material; and
      at least about 5% by weight of a thermosetting or sinterable polymer; and
   at least about 0.05% by weight of a catalytically active metal supported on the catalyst support.

6. The catalyst composite of claim 5, wherein the catalyst composite has a CO adsorption of at least about 50 microliters per gram of the catalyst composite.

7. The catalyst composite of claim 5, wherein the catalytically active metal is supported on the carbonaceous material.

8. The catalyst composite of claim 5 wherein the catalytically active metal comprises a precious metal.

9. The catalyst composite of claim 5, wherein the catalyst composite comprises particles having a crush strength of at least about 1 lbs/mm of particle length.

10. The catalyst composite of claim 5, wherein the catalyst support can be deformed to 80% of its original size in at least one of its dimensions without breaking.

11. The catalyst composite of claim 5, wherein the catalyst composite is non-friable.

12. A packed bed reactor containing the catalyst composite of claim 5.

13. The catalyst composite of claim 5, wherein the catalyst composite is at least one of a hydrogenation catalyst, a rearrangement catalyst, a purification catalyst, a dehydration catalyst, a dehydrogenation catalyst, an oxidation catalyst, a reduction catalyst, a polymerization catalyst, a dehydrocylcization catalyst, a reforming catalyst, a hydrocracking catalyst, and an isomerization catalyst.

14. A process, comprising contacting a feed stream with the catalyst composite of claim 5.

15. The catalyst composite of claim 5, wherein the polymer comprises a fluorocarbon polymer, a polyolefin, a polystyrene, a substituted polystyrene, a polyester, a polyamide, an epoxy, or a polyether.

16. The catalyst composite of claim 15, wherein the polymer comprises a fluorocarbon polymer.

17. The catalyst composite of claim 5, wherein the polymer is sinterable.

18. A method of making a catalyst composite, comprising:
   mixing a carbonaceous material with a thermosetting or sinterable polymer to obtain a mixture;

heating the mixture to sinter or thermoset the polymer and obtain a catalyst support; and supporting a catalytically active metal on the catalyst support to obtain a catalyst composite.

19. The method of claim 18, wherein heating sinters the polymer.

20. The method of claim 18, further comprising forming the mixture.

21. The method of claim 20, wherein the mixture is heated to sinter or thermoset the polymer subsequent to forming.

22. The method of claim 18, wherein the catalyst composite comprises at least about 5% by weight of the activated carbonaceous material and at least about 20% by weight of the polymer.

23. The method of claim 22, wherein the catalyst composite comprises at least about 0.2% by weight of the catalytically active metal.

24. The method of claim 22, wherein the catalyst composite provides a CO adsorption of at least about 50 microliters per gram of the catalyst composite.

25. A method of making a catalyst composite, comprising:

supporting a catalytically active metal on a carbonaceous material;

mixing the carbonaceous material, having the catalytically active metal supported thereon, with a thermosetting or sinterable polymer to form a mixture; and heating the mixture to sinter or thermoset the polymer.

26. The method of claim 25, wherein heating the mixture sinters the polymer.

27. The method of claim 25, further comprising forming the mixture.

28. The method of claim 27, wherein the mixture is heated to sinter the polymer subsequent to forming.

29. The method of claim 25, wherein the catalyst composite comprises at least about 5% by weight of the activated carbonaceous material and at least about 20% by weight of the polymer.

30. The method of claim 29, wherein the catalyst composite comprises at least about 0.2% by weight of the catalytically active metal.

31. The method of claim 25, wherein the catalyst composite provides a CO adsorption of at least about 50 microliters per gram of the catalytically active metal at STP.

32. A method of obtaining a purified crude polycarboxylic aromatic acid composition, comprising:

contacting the crude polycarboxylic aromatic acid composition, or an ester precursor thereof, with a catalyst composite according to claim 5.

33. The method of claim 32, wherein the crude polycarboxylic aromatic acid composition comprises terephthalic acid, isophthalic acid and 2,6-naphthalene dicarboxylic acid.

34. The method of claim 32, wherein the crude polycarboxylic aromatic acid composition comprises terephthalic acid and at least one of undesirable coloring components and 4-carboxy benzaldehyde.

35. The method of claim 32, wherein the catalytically active metal comprises at least one of platinum, rhenium, ruthenium, tungsten, nickel, rhodium, lead, germanium, palladium, cobalt, osmium, and iridium.

36. The method of claim 32, wherein the crude polycarboxylic aromatic acid composition, or ester precursor thereof, is contacted with the catalyst composite at a temperature from about 50° C. to about 350° C. under a pressure from about 150 psig to about 1,600 psig.

37. A method of purifying a crude amine composition or a crude alkynol amine composition, comprising:

contacting the crude amine composition or the crude alkynol amine composition with a catalyst composite according to claim 5.

38. The method of claim 37, wherein the crude amine composition or the crude alkynol amine composition comprises a crude aromatic amine composition, a crude aromatic alkynol amine composition, a crude aliphatic amine composition, or a crude aliphatic alkynol amine composition.

* * * * *